(12) United States Patent
Laskoski et al.

(10) Patent No.: US 9,981,887 B1
(45) Date of Patent: May 29, 2018

(54) SYNTHESIS OF PHENYLETHYNYLBENZENES

(71) Applicant: The United States of America, as represented by the Secretary of the Navy, Washington, DC (US)

(72) Inventors: Matthew Laskoski, Springfield, VA (US); Teddy M. Keller, Fairfax Station, VA (US)

(73) Assignee: The United States of America, as represented by the Secretary of the Navy, Washington, DC (US)

( * ) Notice: Subject to any disclaimer, the term of this patent is extended or adjusted under 35 U.S.C. 154(b) by 0 days. days.

(21) Appl. No.: 15/867,009

(22) Filed: Jan. 10, 2018

Related U.S. Application Data

(60) Provisional application No. 62/444,506, filed on Jan. 10, 2017.

(51) Int. Cl.
  *C07C 2/86* (2006.01)
  *C07C 37/62* (2006.01)
  *C07C 303/28* (2006.01)

(52) U.S. Cl.
  CPC .............. *C07C 2/868* (2013.01); *C07C 37/62* (2013.01); *C07C 303/28* (2013.01); *C07C 2531/22* (2013.01); *C07C 2531/24* (2013.01)

(58) Field of Classification Search
  CPC .. C07D 491/22; C07D 493/22; C07D 495/04; C07D 495/22; C08G 61/02; C08G 61/124; C08G 63/00; C08G 65/002; C08J 9/00; C08J 9/36; C01B 32/00; C01B 32/05
  See application file for complete search history.

(56) References Cited

U.S. PATENT DOCUMENTS

| | | |
|---|---|---|
| 5,980,853 A | 11/1999 | Keller et al. |
| 2003/0028024 A1* | 2/2003 | Rauchschwalbe ... C07D 495/04 544/345 |
| 2013/0046073 A1* | 2/2013 | Goto ................. C08G 61/02 528/8 |
| 2014/0249239 A1* | 9/2014 | Cooper .............. C08G 61/02 521/53 |
| 2016/0315272 A1 | 10/2016 | Youfu et al. |

OTHER PUBLICATIONS

Hassan et al., "Synthesis of tetraaryl-p-benzoquinones and 2,3-diaryl-1,4-naphthoquinones via SuzukieMiyaura cross-coupling reactions" Tetrahedron 69 (2013) 460-469.

Kumar et al., "Copper-catalyzed alkyne-aryne coupling reaction under microwave conditions: preparation of unsymmetric and symmetric di-substituted alkynes" Tetrahedron Letters 50 (2009) 1809-1811.

Livi et al., "Analysis of Diverse Direct Arylation Polymerization (DArP) Conditions Toward the Efficient Synthesis of Polymers Converging with Stille Polymers in Organic Solar Cells" J. of Polym. Sci. A: Polym. Chem. 2016, 54, 2907-2918.

Perpall et al., "Novel Network Polymer for Templated Carbon Photonic Crystal Structures" Langmuir 2003, 19, 7153-7156.

Shirakawa et al., "A simple catalyst system for the palladium-catalyzed coupling of aryl halides with terminal alkynes" Tetrahedron 61 (2005) 9878-9885.

Wittmeyer et al., "Toward Truly Water-Soluble Rodlike Polyelectrolytes: Synthesis of Poly(para-phenylenes) Wrapped in Ethylene Oxide and Amino Side Groups" Macromol. Chem. Phys. 2016, 217, 1473-1487.

* cited by examiner

*Primary Examiner* — Sharon Pregler

(74) *Attorney, Agent, or Firm* — US Naval Research Laboratory; Joseph T. Grunkemeyer

(57) ABSTRACT

A method of: reacting a dihydroxybenzene with bromine to form a bromodihydroxybenzene; reacting the bromodihydroxybenzene with trifluoromethanesulfonyl chloride or trifluoromethanesulfonic anhydride to form a bromotrifluoromethanesulfonatobenzene; and reacting the bromotrifluoromethanesulfonatobenzene with phenylacetylene to form a phenylethynylbenzene.

13 Claims, 1 Drawing Sheet

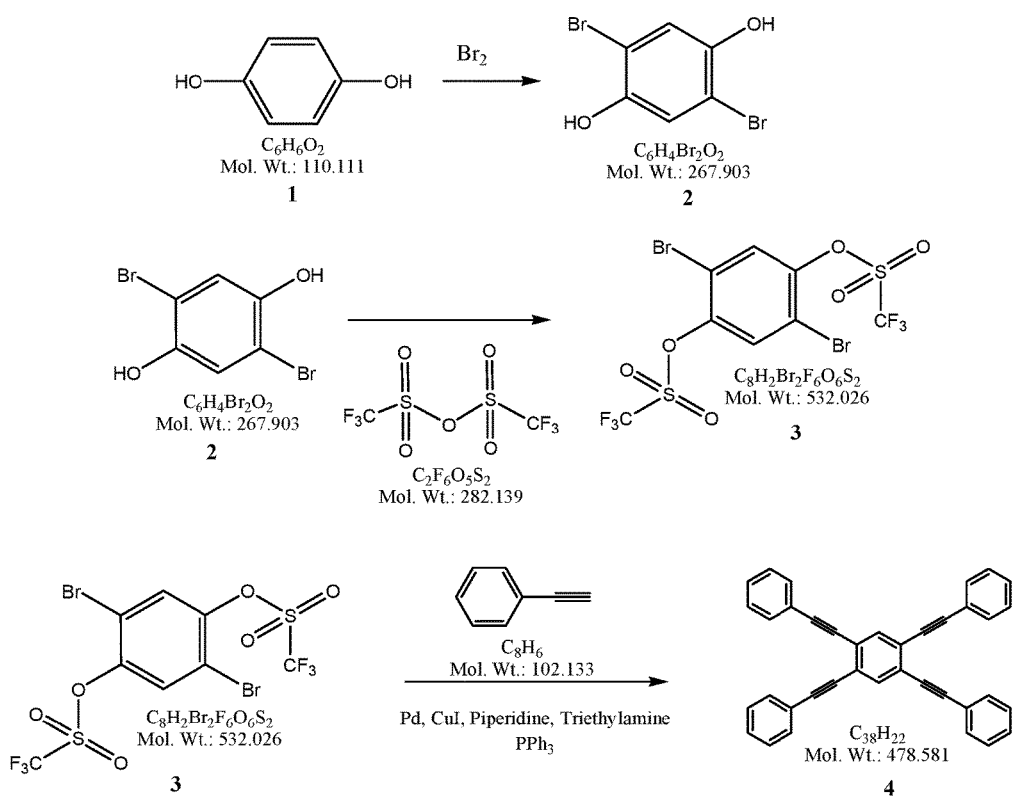

ated materials technologies. The key intermediate to
SYNTHESIS OF PHENYLETHYNYLBENZENES This application claims the benefit of U.S. Provisional Application No. 62/444,506, filed on Jan. 10, 2017. The provisional application and all other publications and patent documents referred to throughout this nonprovisional application are incorporated herein by reference.

TECHNICAL FIELD

The present disclosure is generally related to synthesis of phenylethynylbenzenes.

DESCRIPTION OF RELATED ART

Carbon based materials are desirable because of the high strength and low weight density of carbon. Furthermore, carbon maintains its mechanical properties at high temperatures over 3000° C. under non-oxidizing environments. Other materials, which are used as precursors to carbon, include phenolic resins and petroleum pitches. A problem with the current materials is the loss of substantial amounts of material during processing creating porous, void-containing carbonaceous compositions and thus it is necessary to use multiple impregnations in order to build up the density of the composite components and to enhance the bonding between the fiber and matrix, which adds to the manufacturing cost. Phenolic resins typically afford a 40-45% carbon yield and petroleum pitch is somewhat higher. Both the phenolic and pitches are hard to process into shaped components.

The compound 1,2,4,5-tetrakis(phenylethynyl)benzene (TPEB) and other phenylethynylbenzenes have been synthesized from the corresponding bromobenzenes (U.S. Pat. No. 5,980,853). The bromocompounds are very expensive to directly purchase and are typically used in the synthesis of the phenylethynylbenzenes. The phenylethynylbenzenes polymerized to thermosetting polymers, which yield carbon rich materials upon pyrolysis with extremely high char yields. A distinction of these phenylethynylbenzenes is the structures, which give improved properties as carbon precursors. Upon melting and then pyrolysis to 1000° C., at least 85% of the initial weight is retained for TPEB. The other phenylethynylbenzenes containing less than four phenylethynyl groups did not exhibit the required thermal stability to be useful as a carbon source especially when cured under atmospheric conditions but retained their weight when pyrolyzed under external pressure.

BRIEF SUMMARY

Disclosed herein is a method comprising: reacting a dihydroxybenzene with bromine to form a bromodihydroxybenzene; reacting the bromodihydroxybenzene with a trifluoromethanesulfonyl compound selected from trifluoromethanesulfonyl chloride and trifluoromethanesulfonic anhydride to form a bromotrifluoromethanesulfonatobenzene; and reacting the bromotrifluoromethanesulfonatobenzene with phenylacetylene to form a phenylethynylbenzene.

BRIEF DESCRIPTION OF THE DRAWING

A more complete appreciation will be readily obtained by reference to the following Description of the Example Embodiments and the accompanying drawing.

FIG. 1 shows a scheme for synthesis of 1,2,4,5-tetrakis(phenylethynyl)benzene.

DETAILED DESCRIPTION OF EXAMPLE EMBODIMENTS

In the following description, for purposes of explanation and not limitation, specific details are set forth in order to provide a thorough understanding of the present disclosure. However, it will be apparent to one skilled in the art that the present subject matter may be practiced in other embodiments that depart from these specific details. In other instances, detailed descriptions of well-known methods and devices are omitted so as to not obscure the present disclosure with unnecessary detail.

Disclosed herein is an improved, more cost-effective method for the synthesis of phenylethynylbenzenes and their conversion to the thermoset polymers that serve as precursors to carbon based materials. The starting materials for the new synthetic method are hydroquinone, resorcinol, and catechol, which are very inexpensive when compared to the multiple stepped bromination of various expensive aromatic compounds. 1,2,4,5-Tetrakis(phenylethynyl)benzene (TPEB) is a very important compound in numerous advanced materials technologies. The key intermediate to the improved synthesis of TPEB is the reaction of hydroquinone with selective ortho-dibromination followed by quantitative trifluoromethanesulfonate (triflate) esterification of the two hydroxyl groups, using trifluoromethanesulfonyl chloride ($CF_3$—$SO_2$—Cl) or trifluoromethanesulfonic anhydride ($CF_3$—$SO_2$—O—$SO_2$—$CF_3$) giving the dibromoditriflate intermediates in very high yield. The dibromoditriflate reacts in high yield with phenylacetylene to afford tetrakis(phenylethynyl)benzene. This procedure is adaptable to resorcinol and catechol as the dihydroxybenzene. The bromination of hydroquinone, resorcinol, or catechol can be carried out stepwise in high yield to afford bromination of all of the available sites. The polymers formed from the corresponding phenylethynylbenzenes may be used for the production, upon fusion and then pyrolysis, of materials that have extremely low hydrogen content and consist essentially of carbon. The phenylethynylbenzene compounds can be melted and then easily processed into shaped high temperature thermosetting polymeric materials. Crosslinking of the ethynyl (acetylenic) groups is known to occur by either thermal or photochemical means. The acetylenic-containing compounds (monomers), when melted, exhibit low viscosity when compared with currently used carbon precursor materials such as phenolic resins and petroleum pitches but exhibit high comparative char yields. This inherent property of these materials eliminates the costly multiple carbonization and reimpregnation steps necessary with current technologies for the preparation of carbon-carbon composites. Furthermore, the monomers/prepolymers are soluble in a variety of solvents. Thus, most of the compounds can be molded by conventional procedures into shaped structures at atmospheric pressure because of their low vapor pressure. However, if needed, external pressure can be applied to consolidate to a shaped configuration especially during the polymerization reaction. The monomers/prepolymers can also be processed from solution to produce fibers, coatings, firms, or other shaped articles, which can then be thermally converted to extremely heat resistant carbon articles of the same shape and extremely high char yield.

As currently produced, tetrabromobenzenes are very costly due to multiple steps synthesis and are not produced in significant quantities, as there is not a general market for such compounds. Thus, a better method is needed for their production and their use in the synthesis of the corresponding tetrakis(phenylethynyl)benzenes, which is currently being used in development of several NRL developed materials technologies. The dibromoditriflates are produced from hydroquinone, resorcinol, or catechol, which are widely available in large quantities and are cost effective relative to the current aromatic compounds being used to produce the tetrabromobenzenes. Numerous new material technologies are based on TPEB. Extremely important material applications of the TPEBs are as carbon matrices for carbon-carbon composites, precursor to shaped carbon nanotube (single walled carbon nanotubes and multi-walled carbon nanotubes), and precursor as the source of the carbon in the fabrication of refractory ceramics (carbide, boride, silicide, and nitride) of group IV-VI in the periodic table, silicon carbide/nitride, and boron carbide/nitride. Desirable properties of the carbon precursors are the low viscosity observed initially in the melt phase, ease of conversion to the shaped thermoset, and the high char yield obtained upon pyrolysis. Low viscosity materials are preferred because of the fabrication of components by low-cost manufacturing techniques and their ease of impregnating and wetting of carbon and ceramic fibers. Typically, low viscosity polymeric materials, such as phenolic resins, contain a significant fraction of volatile low molecular weight components. These volatile components contribute to the lower char yields of these systems.

Bromoditriflate intermediates containing 1 to 4 bromo substituents can be readily synthesized in high yield from hydroquinone 1 (FIG. 1), resorcinol, or catechol, which are readily available. The hydroxyl groups of hydroquinone, resorcinol, and catechol are ortho and para directing pertaining to the substitution of bromine onto the benzene ring. Moreover, the bromo group can be added stepwise in high yield to afford the desired brominated compound 2 followed by quantitative trifluoromethane sulfonate (triflate) esterification of the corresponding hydroxyl group. The reaction of the aryl dibromide ditriflate 3 with phenylacetylene in the presence of a palladium catalyst and triethylamine as base afforded greater than 85% yield of the tetrakis(phenylethynyl) benzene 4. Starting from either hydroquinone 1, resorcinol, or catechol, the overall yield is at least 75%. More importantly, the reactions are clean with minor to no purification of the intermediate compounds. The reaction scheme for the synthesis of 1,2,4,5-tetrakis(phenylethynyl) benzene (TPEB) from hydroquinone is shown in FIG. 1.

Acetylenic-based compounds that can be produced from hydroquinone, resorcinol, or catechol include 1,2,4,5-tetrakis(phenylethynyl)benzene; 1,2,3- and 1,2,4-tris(phenylethynyl)benzene; 1,2,3,4- and 1,2,3,5-tetrakis(phenylethynyl)benzene; 1,2,3,4,5-pentakis(phenylethynyl)benzene; and 1,2,3,4,5,6-hexakis(phenylethynyl)benzene. When an excess of diphenol is used, such as a 2:1 molar ratio of diphenol to bromine atoms, a 1,2,4-trisubstituted benzene is the major product, while small amounts of 1,2,3-substituted benzene and higher substitutions are also formed, depending on the starting diphenol. In the case of resorcinol, the addition of bromine meta to both hydroxyl groups is highly disfavored. Table 1 shows the products for each of the diphenols. These products may be separated by distillation, chromatography, or other methods to form pure tris(phenylethynyl)benzenes, or may be kept as a blend for making mixtures of tris(phenylethynyl)benzenes.

TABLE 1

Formation of trisubstituted benzenes

| Reactant | Major product | Minor product |
|---|---|---|
| hydroquinone (1,4-diOH) | 2-Br-1,4-diOH | |
| resorcinol (1,3-diOH) | 4-Br-1,3-diOH | 2-Br-1,3-diOH |
| catechol (1,2-diOH) | 4-Br-1,2-diOH | 3-Br-1,2-diOH |

Likewise, 1,2,4,5-tetrasubstituted benzenes are the major product using any of the diphenols and sufficient bromine, with some 1,2,3,4- and 1,2,3,5-substituted products formed, as shown in Table 2. Addition of further bromine produces 1,2,3,4,5- and 1,2,3,4,5,6-substituted benzenes, as shown in Table 3. Any of the compounds in Tables 1-3 may be used in pure form, as formed in mixtures produced by the reactions described herein, or in any other proportions. All of these compounds will react in the same way as shown in FIG. 1. The hydroxyl groups are substituted by triflate groups, and the bromo and triflate groups are substituted by phenylethynyl groups.

TABLE 2

Formation of tetrasubstituted benzenes

| Reactant | Major product | Minor product | Minor product |
|---|---|---|---|
| hydroquinone | 2,5-diBr-1,4-diOH | 2,3-diBr-1,4-diOH | |

TABLE 2-continued

Formation of tetrasubstituted benzenes

| Reactant | Major product | Minor product | Minor product |
|---|---|---|---|
| resorcinol (1,3-diOH) | 4,6-dibromo-1,3-benzenediol | 2,4-dibromo-1,3-benzenediol | |
| catechol (1,2-diOH) | 4,5-dibromo-1,2-benzenediol | 3,5-dibromo-1,2-benzenediol | 3,4-dibromo-1,2-benzenediol |

TABLE 3

Formation of penta- and hexasubstituted benzenes

| Reactant | Products |
|---|---|
| hydroquinone (1,4-diOH) | 2,3,5-tribromo-1,4-benzenediol; 2,3,5,6-tetrabromo-1,4-benzenediol |
| resorcinol (1,3-diOH) | 2,4,6-tribromo-1,3-benzenediol; 2,4,5,6-tetrabromo / 4,5,6-tribromo isomers; tetrabromo-1,3-benzenediol |
| catechol (1,2-diOH) | 3,4,5-tribromo-1,2-benzenediol; 3,4,5,6-tetrabromo isomers |

These substances can be easily processed into void-free films or shaped components in a controlled manner by the conventional melt processing. The polymerization reaction can then be initiated by heating the melt to a higher temperature until gelation occurs as determined by differential scanning calorimetry (DSC). The monomers upon cure afford void-free thermosetting polymeric materials. The polymers upon pyrolysis to 1000° C. show at least 85% weight retention as determined by thermo-gravimetric analysis (TGA). Because of the high weight retention, the acetylenic-based aromatic compounds especially 1,2,4,5-tetrakis(phenylethynyl)benzene has been used in the fabrication of carbon nanotubes in shaped solids and as the carbon sources in the synthesis and development of ultra-high temperature refractory ceramics and carbon-carbon composites. The acetylenic-based monomers and prepolymers (B-staged) can be stored indefinitely at room temperature.

Acetylenic-based compounds such as 4 and other phenylethynylbenzenes produced by the bromoditriflate intermediates can be readily produced in three steps starting from hydroquinone, resorcinol, or catechol. The synthetic method yields high yields of the phenylethynylbenzenes, which is in contrast to the prior method involving the synthesis and availability of the corresponding bromobenzenes and their reaction with phenylacetylene. The starting materials for the synthesis of the various bromobenzenes are not always readily available and are typically more expensive than the hydroquinone, resorcinol, and catechol. Numerous lower yielding reactions are needed to produce the various bromobenzenes followed by purification. As stated previously, 1,2,4,5-tetrakis(phenylethynyl)benzene 4 is a compound useful for numerous advanced materials and a better method of production is needed for transition to applied applications. For example, carbon-carbon (C—C) composites are being used for numerous structural applications at elevated temperatures because of their light weight, high strength, high modulus, low coefficient of thermal expansion, and thermal stability. The matrices in C—C composites are either derived from hard, glassy-like carbons or soft, graphitizing carbons. The glassy carbons are typically formed from thermosetting polymers such as phenolic resin, cellulose, polyfurfuryl alcohol, and the polyarylacetylenes. The phenolic resin is most commonly used due to its low-cost. However, processing problems are associated with the phenolic resin including a low char yield (40-45%) from the presence of high percentage of oxygen and the formation of water and the large amount of shrinkage during carbonization. The evolution of water results in a high percentage of void formation necessitating multi-step redensification until the proper density is achieved. Pitch is the most common, commercially available precursor material for soft, graphitizing carbon. It undergoes a liquid crystalline transformation (mesophase) between 400° C. and 550° C., which enables alignment of the large aromatic molecules that are precursors to graphite. Pitch is very difficult to work with because of the high viscosity, the need for high-pressure equipment, and the batch-to-batch inconsistencies. As derived from petroleum residues, pitch is composed of a complex mixture of aromatic hydrocarbons with 3-8 condensed rings and an average molecular weight of 300. Pitch results in a high char yield only if carbonization is performed very slowly or under high pressure of up to 100 bars. The thermosetting resins derived from the phenylethynylbenzenes do not need pressure carbonization.

In contrast to phenolic resins and petroleum pitches, the carbon-precursor (phenylethynyl)benzenes can be directly carbonized to void-free components. Thus, a better, more cost-effective method is needed to produce the phenylethynylbenzenes. Because these compounds are pure substances, they have definite melting points and well defined gelation temperature/time characteristics. For example, the melting point of 4 is approximately 194° C., and the temperature at which onset of crosslinking occurs is about 230-240° C.; thus this compound has a good processing window. Furthermore, both low molecular weight (possibly volatile) and high molecular weight (possibly insoluble and high melting) components of a hypothetical polymer mixture are absent. The acetylenic-based monomers can be prepared in a single step reaction between phenylacetylene, the brominated ditriflate, amine base, and palladium catalyst.

The ability to produce the TPEB 4 from common chemical that are readily available and the simplicity of the reaction scheme enhance the importance of 4 as an easily processability carbon sources carbon-carbon composites, for the carbon nanotubes (fibers and shaped solids) and for the refractory ultra-high temperature refractory ceramics. The yield of forming the phenylethynylbenzenes starting from either hydroquinone, resorcinol or catechol is in excess of 75%.

The following examples are given to illustrate specific applications. These specific examples are not intended to limit the scope of the disclosure in this application.

Example 1

Synthesis of 1,4-dibromo-2,5-dihydroxybenzene from Hydroquinone

To a 1 L three neck flask, equipped with a nitrogen gas inlet and a gas outlet attached to a bubbler containing an aqueous sodium hydroxide solution (7.26 g NaOH in 300 mL water) and a dropping funnel, was placed hydroquinone (20 g, 182 mmol) in 200 mL of glacial acetic acid. The flask was placed in an ice bath and the nitrogen flow started. Bromine (60.9 g, 381 mmol) was added dropwise over a 20 min period. During this time, a white solid precipitated from the solution followed by stirring of the reaction mixture at room temperature for 12 h. After cooling in an ice bath, the reaction content was filtered and washed with cold water until neutral. The white solid product, 1,4-dibromo-2,5-dihydroxybenzene (41.4 g, 85%), was dried under vacuum. $^1$H NMR (300 MHz, CDCl$_3$): δ 7.14 (2H, s), 5.2 (2H, br, s).

Example 2

Synthesis of 1,4-dibromo-2,5-bis(trifluoromethanesulfonato)benzene

The bisphenol from Example 1 (10.0 g, 37.3 mmol) was dissolved in 100 mL of dry methylene chloride and then dry triethylamine (9.44 g, 13.0 mL, 93.6 mmol) was added. The mixture was cooled in an ice bath and trifluoromethanesulfonyl chloride (13.2 g, 8.4 mL, 78.4 mmol) was added dropwise over 10 minutes. The reaction mixture was stirred for three hours followed by transferring to a separatory funnel, and then washed with aqueous 5% HCl (50 mL), saturated sodium bicarbonate solution (50 mL), and two portions of water (100 mL each). The organic layer was collected, dried over anhydrous MgSO$_4$ and the solvent removed in vacuo to yield 1,4-dibromo-2,5-bis(trifluoromethanesulfonato)benzene (19.3 g, 97%) as a white solid. $^1$H NMR (300 MHz, CDCl$_3$): δ 7.67 (2H, s).

Example 3

Synthesis of 1,4-dibromo-2,5-bis(trifluoromethanesulfonato)benzene

The bisphenol from Example 1 (10.0 g, 37.3 mmol) was dissolved in 100 mL of dry methylene chloride and then dry triethylamine (9.44 g, 13.0 mL, 93.6 mmol) was added. The mixture was cooled in an ice bath and trifluoromethanesulfonic anhydride (23.2 g, 13.8 mL, 82.1 mmol) was added dropwise over 10 minutes. The reaction mixture was stirred for three hours followed by transferring to a separatory funnel and then washed with aqueous saturated sodium bicarbonate solution (2×100 mL) and two portions of water (100 mL each). The organic layer was collected, dried over anhydrous MgSO$_4$ and the solvent was removed in vacuo to yield the crude solid. The crude solid was dissolved in 100 mL of acetonitrile and extracted with three 100 mL portion of hexanes. The hexanes layers were collected, dried and evaporated to yield 1,4-dibromo-2,5-bis(trifluoromethanesulfonato)benzene (17.9 g, 90%) as a tan solid. $^1$H NMR (300 MHz, CDCl$_3$): δ 7.67 (2H, s).

Example 4

Synthesis of 1,2,4,5-tetrakis(phenylethynyl)benzene from 1,4-dibromo-2,5-bis(trifluoromethanesulfonato)benzene To a 500 mL, three-necked flask fitted with a thermometer, condenser, and a nitrogen inlet were added DMF (100 mL) and piperidine (100 mL) under nitrogen, and the solvents were purged thoroughly with nitrogen for 15 min. Then 1,4-dibromo-2,5-bis(trifluoromethanesulfonato)benzene from Example 2 or 3 (10 g, 18.8 mmol) and nitrogen degassed phenylacetylene (8.6 g, 9.3 mL, 85 mmol) were added. This reaction is very oxygen sensitive. Once the reaction is completely purged free of oxygen, dichlorobis (triphenylphosphine)palladium (II) ($Cl_2Pd(PPh_3)_2$) (0.650 g, 0.05 mmol) was added. The reaction mixture was heated slowly to 100° C. and after stirring from several minutes to hours, the reaction mixture became very viscous from the formation of the solid piperidinium HCl salt. (NOTE: This part of the reaction can be extremely exothermic so much so as to completely vaporize the solvent. Care must be taken to manage heat evolution. The catalyst concentration can be reduced to help reduce the speed of the reaction but the reaction time for completion will be extended. Additionally, it is okay if the reaction completely solidifies and stops stirring at this stage.) Once completed, the reaction is cooled, dumped and broken up in a vigorously stirred 5% aqueous HCl. The solid product was then collected using a Buchner funnel using qualitative filter paper (e.g. Whatman #1), washed with copious amounts of water to remove any excess base and salts, and then dried. The isolated solid may be purified by either recrystallization in an ethanol/$CHCl_3$ or ethanol/ethyl acetate mixture. Filtration followed by drying yielded 1,2,4,5-tetrakis(phenylethynyl)benzene (8.5 g, 95%) as a yellow to brown crystalline solid. Melting Point: 194-196° C. $^1$H-NMR (300 MHz, $CDCl_3$): δ 7.76 (s, aromatic-2H), 7.56-7.51 (m, aromatic-8H), 7.37-7.30 (m, aromatic-12H). $^{13}$C-NMR (300 MHz, $CDCl_3$): δ 134.85, 131.70, 128.69, 128.40, 125.29, 122.93 (aromatic), 95.45, 87.54 (alkyne).

Example 5

Synthesis of 1,5-dibromo-2,4-dihydroxybenzene from resorcinol

To a 1 L, three neck flask, equipped with a nitrogen gas inlet and a gas outlet attached to a bubbler containing aqueous sodium hydroxide solution (7.26 g NaOH in 300 mL water) and a dropping funnel, was placed resorcinol (20 g, 182 mmol) in 200 mL of glacial acetic acid. The flask was placed in an ice bath and the nitrogen flow was started. Bromine (60.9 g, 381 mmol) was added dropwise over a 20 min period. During this time, a white solid precipitated from the solution and the reaction was stirred at room temperature for 12 h. The reaction flask was then cooled in an ice bath and the reaction mixture was filtered and washed with cold water until neutral. The white solid product composed of a mixture of 1,5-dibromo-2,4-dihydroxybenzene and other isomers (42 g, 87%) was dried under vacuum. $^1$H NMR (300 MHz, $CDCl_3$): δ 7.3-7.1 (2H, m), 5.3 (2H, br, s).

Example 6

Synthesis of 1,5-dibromo-2,4-bis(trifluoromethanesulfonato)benzene

The bisphenol from Example 5 (10.0 g, 37.3 mmol) was dissolved in 100 mL of dry methylene chloride and then dry triethylamine (9.44 g, 13.0 mL, 93.6 mmol) was added. The mixture was cooled in an ice bath and trifluoromethanesulfonyl chloride (13.2 g, 8.4 mL, 78.4 mmol) was added dropwise over 10 minutes. The reaction mixture was stirred for three hours followed by transferring to a separatory funnel and then washed with aqueous 5% HCl (50 mL), saturated sodium bicarbonate solution (50 mL), and two portion of water (100 mL each). The organic layer was collected, dried over anhydrous $MgSO_4$ and the solvent was removed in vacuo to yield 1,5-dibromo-2,4-bis(trifluoromethanesulfonato)benzene and other isomers (19.5 g, 98%) as a white solid. $^1$H NMR (300 MHz, $CDCl_3$): δ 7.60-7.50 (2H, m).

Example 7

Synthesis of 1,5-dibromo-2,4-bis(trifluoromethanesulfonato)benzene

The bisphenol from Example 5 (10.0 g, 37.3 mmol) was dissolved in 100 mL of dry methylene chloride and then dry triethylamine (9.44 g, 13.0 mL, 93.6 mmol) was added. The mixture was cooled in an ice bath and trifluoromethanesulfonic anhydride (23.2 g, 13.8 mL, 82.1 mmol) was added dropwise over 10 minutes. The reaction mixture was stirred for three hours followed by transferring to a separatory funnel and then washed with aqueous saturated sodium bicarbonate solution (2×100 mL) and two portions of water (100 mL each). The organic layer was collected, dried over anhydrous $MgSO_4$ and the solvent was removed in vacuo to yield the crude solid. The crude solid was dissolved in 100 mL of acetonitrile and extracted with three 100 mL portion of hexanes. The hexanes layers were collected, dried, and evaporated to yield 1,5-dibromo-2,4-bis(trifluoromethanesulfonato)benzene and other isomers (18.4 g, 93%) as a tan solid. $^1$H NMR (300 MHz, $CDCl_3$): δ 7.70-7.50 (2H, m).

Example 8

Synthesis of 1,2,4,5-tetrakis(phenylethynyl)benzene from 1,5-dibromo-2,4-bis(trifluoromethanesulfonato)benzene Mixture To a 500 mL, three-necked flask fitted with a thermometer, condenser, and a nitrogen inlet were added DMF (100 mL) and piperidine (100 mL) under nitrogen and the solvents purged thoroughly with nitrogen for 15 min. Then 1,5-dibromo-2,4-bis(trifluoromethanesulfonato)benzene and the other isomer mixture from Example 6 or 7 (10 g, 18.8 mmol) and nitrogen degassed phenylacetylene (8.6 g, 9.3 mL, 85 mmol) were added. This reaction is very oxygen sensitive. Once the reaction mixture is completely inert and oxygen is removed, dichlorobis(triphenylphosphine)palladium (II) ($Cl_2Pd(PPh_3)_2$) (0.650 g, 0.05 mmol) was added. The reaction mixture was carefully heated slowly to 100° C. and after stirring for several minutes to hours, the reaction mixture became very viscous to completely solid from the formation of the piperidinium HCl salt. (NOTE: This part of the reaction can be extremely exothermic so much so as to completely vaporize the solvent. Care must be taken to manage heat evolution. The catalyst concentration can be reduced to reduce the speed of the reaction but the reaction time for completion will be extended. Additionally, it is okay if reaction completely solidifies and stops stirring at this stage.) Once completed, the reaction is cooled, dumped and broken up in a vigorously stirred 5% aqueous HCl. The solid product was then collected using a Buchner funnel and qualitative filter paper (e.g. Whatman #1), washed with copious amounts of water to remove any excess base and salts, and then dried. The isolated solid product is purified by either recrystallization of an ethanol/$CHCl_3$ or ethanol/ethyl acetate mixture. Filtration followed by drying yielded 1,2, 4,5-tetrakis(phenylethynyl)benzene (7.15 g, 81%) and other isomers (0.975 g, 12%) as a yellow to brown crystalline solid. $^1$H-NMR (300 MHz, CDCl$_3$): δ 7.80-7.75 (m, aromatic-2H), 7.56-7.51 (m, aromatic-8H), 7.37-7.30 (m, aromatic-12H).

Example 9

Synthesis of 1,2-dibromo-4,5-dihydroxybenzene from Catechol

To a 1 L, three neck flask, equipped with a nitrogen gas inlet and a gas outlet attached to a bubbler containing an aqueous sodium hydroxide solution (7.26 g NaOH in 300 mL water) and a dropping funnel, was placed catechol (20 g, 182 mmol) in 200 mL of glacial acetic acid. The flask was placed in an ice bath and the nitrogen flow started. Bromine (60.9 g, 381 mmol) was added dropwise over a 20 min period. During this time, a white solid precipitated from solution and the reaction mixture was stirred at room temperature for 12 h. The reaction flask was then cooled in an ice bath and the reaction filtered and washed with cold water until neutral. The white solid containing a mixture of 1,2-dibromo-4,5-dihydroxybenzene and other isomers (42 g, 87%) was dried under vacuum. $^1$H NMR (300 MHz, CDCl$_3$): δ 7.41-7.10 (2H, m), 5.31 (2H, br, s).

Example 10

Synthesis of 1,2-dibromo-4,5-bis(trifluoromethanesulfonato)benzene

The bisphenol from Example 9 (10.0 g, 37.3 mmol) was dissolved in 100 mL of dry methylene chloride and then dry triethylamine (9.44 g, 13.0 mL, 93.6 mmol) was added. The mixture was cooled in an ice bath and trifluoromethanesulfonyl chloride (13.2 g, 8.4 mL, 78.4 mmol) was added dropwise over 10 minutes. The reaction mixture was stirred for three hours followed by transferring to a separatory funnel and then washed with aqueous 5% HCl (50 mL), saturated sodium bicarbonate solution (50 mL), and two portions of water (100 mL each). The organic layer was collected, dried over anhydrous MgSO$_4$ and the solvent was removed in vacuo to yield 1,2-dibromo-4,5-bis(trifluoromethanesulfonato)benzene and other isomers (19.5 g, 98%) as a white solid. $^1$H NMR (300 MHz, CDCl$_3$): δ 7.60-7.50 (2H, m).

Example 11

Synthesis of 1,2-dibromo-4,5-bis(trifluoromethanesulfonato)benzene

The bisphenol from Example 9 (10.0 g, 37.3 mmol) was dissolved in 100 mL of dry methylene chloride and then dry triethylamine (9.44 g, 13.0 mL, 93.6 mmol) was added. The mixture was cooled in an ice bath and trifluoromethanesulfonic anhydride (23.2 g, 13.8 mL, 82.1 mmol) was added dropwise over 10 minutes. The reaction mixture was stirred for three hours followed by transferring to a separatory funnel and then washed with aqueous saturated sodium bicarbonate solution (2×100 mL) and two portion of water (100 mL each). The organic layer was collected, dried over anhydrous MgSO$_4$ and the solvent was removed in vacuo to yield the crude solid product. The crude solid was dissolved in 100 mL of acetonitrile and extracted with three 100 mL portion of hexanes. The hexanes layers were collected, dried and evaporated to yield 1,2-dibromo-4,5-bis(trifluoromethanesulfonato)benzene and other isomers (18.0 g, 91%) as a tan solid. $^1$H NMR (300 MHz, CDCl$_3$): δ 7.75-7.52 (2H, m).

Example 12

Synthesis of 1,2,4,5-tetrakis(phenylethynyl)benzene from 1,2-dibromo-4,5-bis(trifluoromethanesulfonato)benzene Mixture To a 500 mL, three-necked flask fitted with a thermometer, condenser, and a nitrogen inlet were added DMF (100 mL) and piperidine (100 mL) under nitrogen and the solvents purged thoroughly with nitrogen for 15 min. Then 1,2-dibromo-4,5-bis(trifluoromethanesulfonato)benzene and the other isomer mixture from Example 10 or 11 (10 g, 18.8 mmol) and nitrogen degassed phenylacetylene (8.6 g, 9.3 mL, 85 mmol) were added. This reaction is very oxygen sensitive. Once the reaction is completely inert and the oxygen is removed, dichlorobis(triphenylphosphine)palladium (II) (Cl$_2$Pd(PPh$_3$)$_2$) (0.650 g, 0.05 mmol) was added. The reaction mixture was carefully heated slowly to 100° C. and after stirring several minutes to hours, the reaction mixture became very viscous to completely solid from the formation of the piperidinium HCl salt. (NOTE: This part of the reaction can be extremely exothermic so much so as to completely vaporize the solvent. Care must be taken to manage heat evolution. The catalyst concentration can be reduced to reduce the speed of the reaction but the reaction time will be extended. Additionally, it is okay if reaction completely solidifies and stops stirring at this stage.) Once completed, the reaction was cooled, dumped, and broken up in a vigorously stirred 5% aqueous HCl. The solid product was then collected using a Buchner funnel and qualitative filter paper (e.g. Whatman #1), washed with copious amounts of water to remove any excess base and salts, and then dried. The isolated solid is purified by either recrystallization of an ethanol/CHCl$_3$ or ethanol/ethyl acetate mixture. Filtration followed by drying yielded 1,2,4,5-tetrakis (phenylethynyl)benzene (7.08 g, 80%) and other isomers (1.04 g, 13%) as a yellow to brown crystalline solid. $^1$H-NMR (300 MHz, CDCl$_3$): δ 7.80-7.75 (m, aromatic-2H), 7.56-7.51 (m, aromatic-8H), 7.37-7.30 (m, aromatic-12H).

Obviously, many modifications and variations are possible in light of the above teachings. It is therefore to be understood that the claimed subject matter may be practiced otherwise than as specifically described. Any reference to claim elements in the singular, e.g., using the articles "a", "an", "the", or "said" is not construed as limiting the element to the singular.

What is claimed is:

1. A method comprising:
reacting a dihydroxybenzene with bromine to form a bromodihydroxybenzene;
reacting the bromodihydroxybenzene with a trifluoromethanesulfonyl compound selected from trifluoromethanesulfonyl chloride and trifluoromethanesulfonic anhydride to form a bromotrifluoromethanesulfonatobenzene; and
reacting the bromotrifluoromethanesulfonatobenzene with phenylacetylene to form a phenylethynylbenzene.

2. The method of claim 1, wherein the dihydroxybenzene is hydroquinone.

3. The method of claim 1, wherein the dihydroxybenzene is resorcinol.

4. The method of claim 1, wherein the dihydroxybenzene is catechol.

5. The method of claim 1, wherein the bromodihydroxybenzene is 1,4-dibromo-2,5-dihydroxybenzene.

6. The method of claim 1, wherein the bromodihydroxybenzene is 1,5-dibromo-2,4-dihydroxybenzene.

7. The method of claim 1, wherein the bromodihydroxybenzene is 1,2-dibromo-4,5-dihydroxybenzene.

8. The method of claim 1, wherein the trifluoromethanesulfonyl compound is trifluoromethanesulfonyl chloride.

9. The method of claim 1, wherein the trifluoromethanesulfonyl compound is trifluoromethanesulfonyl anhydride.

10. The method of claim 1, wherein the bromotrifluoromethanesulfonatobenzene is 1,4-dibromo-2,5-bis(trifluoromethanesulfonato)benzene.

11. The method of claim 1, wherein the bromotrifluoromethanesulfonatobenzene is 1,5-dibromo-2,4-bis(trifluoromethanesulfonato)benzene.

12. The method of claim 1, wherein the bromotrifluoromethanesulfonatobenzene is 1,2-dibromo-4,5-bis(trifluoromethanesulfonato)benzene.

13. The method of claim 1, wherein the phenylethynylbenzene is 1,2,4,5-tetrakis(phenylethynyl)benzene.

\* \* \* \* \*